United States Patent [19]

Bazell et al.

[11] 4,370,987

[45] Feb. 1, 1983

[54] MEDICAL FLUID COLLECTION DEVICE

[76] Inventors: Seymour Bazell, 9235 N. Latrobe, Skokie, Ill. 60077; Edward M. Goldberg, 225 Maple Hill Rd., Glencoe, Ill. 60022

[21] Appl. No.: 194,872

[22] Filed: Oct. 7, 1980

[51] Int. Cl.³ ............................................. A61B 5/14
[52] U.S. Cl. .................................. 128/760; 128/765; 128/218 PA
[58] Field of Search ............... 128/764, 765, 766, 760, 128/276, 218 R, 218 P, 218 PA, 218 DA, 218 N, 218 NV, 221, 220, 215

[56] References Cited

U.S. PATENT DOCUMENTS

| | | | |
|---|---|---|---|
| 3,797,487 | 3/1974 | Schmidt | 128/218 R |
| 3,835,835 | 9/1974 | Thompson et al. | 128/765 X |
| 3,930,492 | 1/1976 | Hatsuno et al. | 128/764 |
| 4,009,716 | 3/1977 | Cohen | 128/218 DA |
| 4,011,868 | 3/1977 | Friend | 128/218 P |
| 4,192,320 | 3/1980 | Megahed | 128/764 |
| 4,216,782 | 8/1980 | Sarstedt | 128/765 |

FOREIGN PATENT DOCUMENTS 873458 6/1971 Canada ...................... 128/218 DA

*Primary Examiner*—John D. Yasko
*Attorney, Agent, or Firm*—Hume, Clement, Brinks, Willian & Olds, Ltd.

[57] ABSTRACT

A medical fluid collection system includes a double ended needle having a disc secured thereto. A resilient elastomeric sleeve is secured to the disc to extend around a portion of the needle, and a pierceable translucent plug is secured to the sleeve such that the plug is situated over one end of the needle in an extended position to prevent fluids from leaking therefrom. This plug is preferably provided with a convex outer surface adjacent the one end of the needle and is moveable along the needle to a retracted position in which the one end of the needle extends out of the plug. The sleeve acts to bias the plug into the extended position. A fluid collection device includes a barrel which defines a bore. A piston is slidingly and sealingly positioned in the bore, and a pierceable diaphragm is provided to seal an interior volume of the bore between the piston and the diaphragm. The diaphragm defines a recess shaped to receive and position the outer surface of the plug such that, when the plug is positioned in the recess and the barrel is urged toward the disc, the one end of the needle passes through the plug and the diaphragm into the interior volume of the barrel. In addition, a rod or cord is attached to the piston to extend outside of the barrel, and locking members are provided on the barrel to lock the rod or cord in position. The rod or cord and the locking members are used to develop a vacuum inside the barrel to aid in drawing fluids through the double ended needle.

40 Claims, 11 Drawing Figures

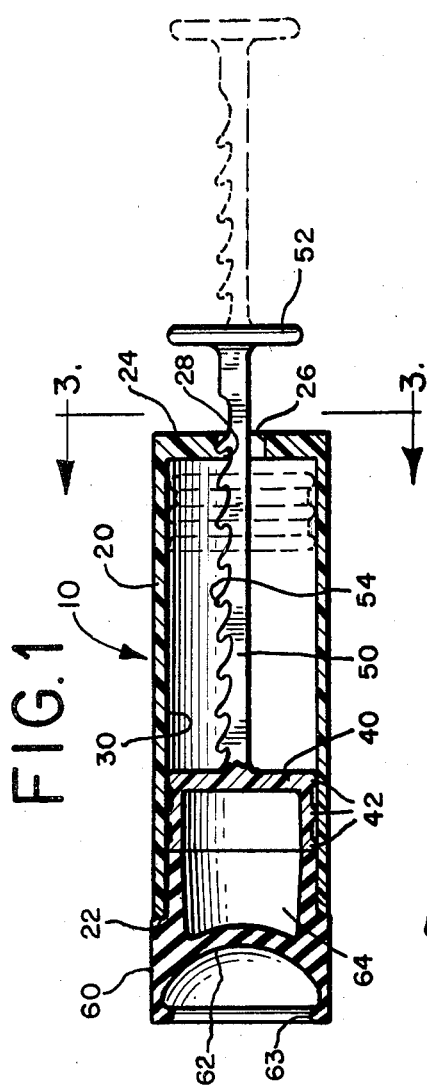
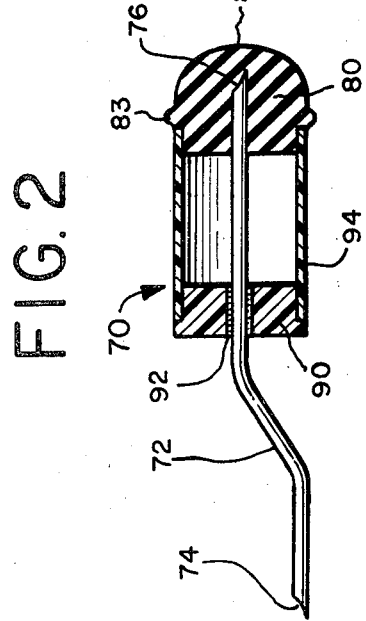
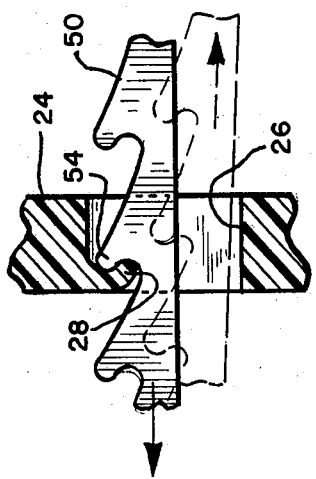
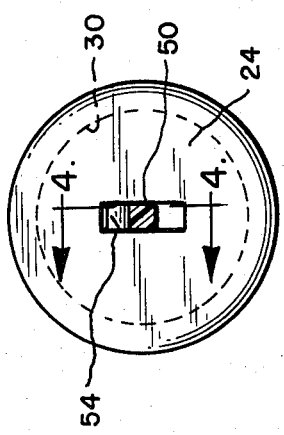
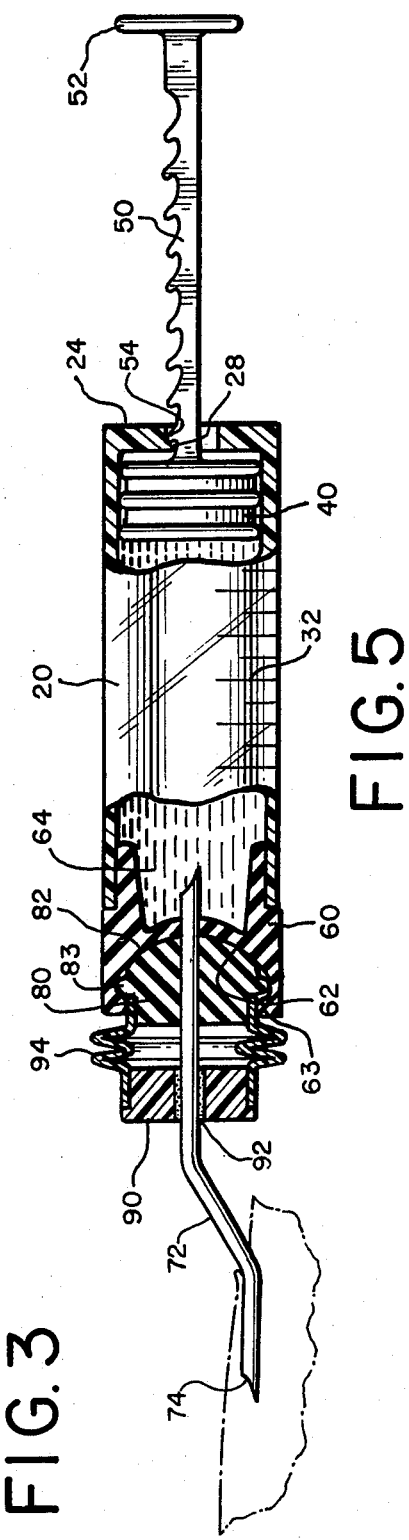

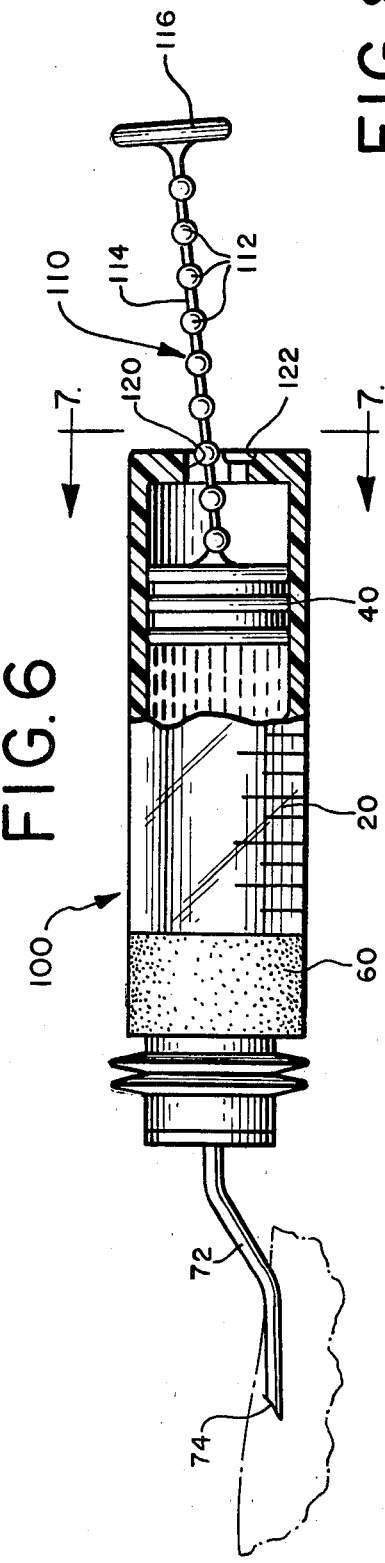
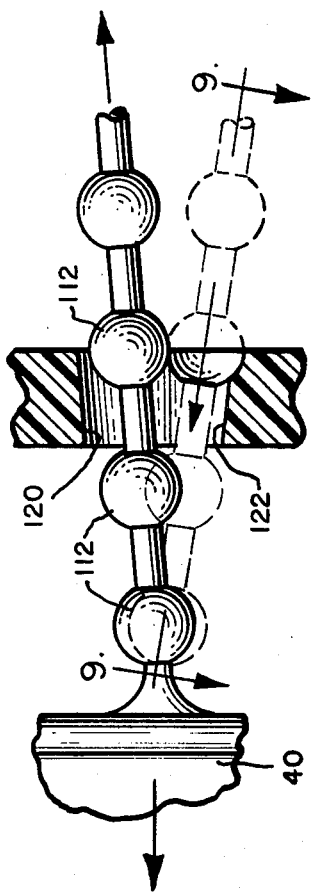
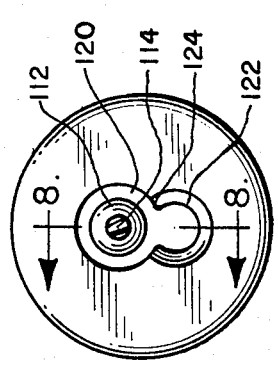
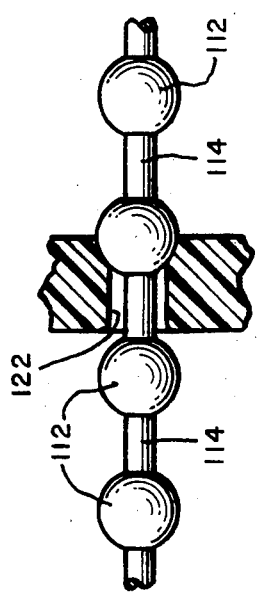
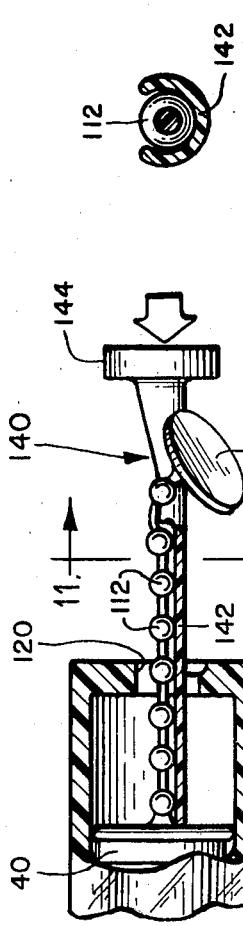

MEDICAL FLUID COLLECTION DEVICE

BACKGROUND OF THE INVENTION

The present invention relates to improved devices for collecting body fluids such as blood, for example.

Blood collection is a routine aspect of medical diagnosis and treatment. It has been found that it is often preferable to provide a collection chamber which is at least partly evacuated to facilitate collection of blood samples. The subatmospheric pressure of the chamber serves as an aid to draw blood from the patient through a conduit, such as a needle for example, into the collection chamber. In the past, it has been common practice to provide pre-evacuated chambers for the collection of blood samples.

Such pre-evacuated chambers are sold as partially evacuated glass tubes which are closed by a pierceable diaphragm. In use, a double-ended needle is placed with one end in a patient's vein and then the other end of the double-ended needle is passed through the pierceable diaphragm into the interior of the collection tube. Subatmospheric pressure inside the tube then acts to draw blood through the needle into the tube.

The use of such pre-evacuated chambers brings with it certain disadvantages. Because the tubes must be stored for extended periods of time after they have been evacuated, it is possible for a slow air leak to destroy the vacuum in the chamber over an extended period of time. Such leakage can result in contamination of the tube when contaminants are brought into the tube by the leaking air. In addition, such leakage presents a reliability problem, because once the vacuum inside the tube is lost the tube must be discarded. Moreover, the vacuum in pre-evacuated collection tubes cannot be adjusted for collection of differing amounts of blood. Thus, it is often necessary to supply and stock several sizes of collection tubes to accomodate the varying needs.

SUMMARY OF THE INVENTION

The present invention is directed to an improved medical fluid collection device which overcomes these and other disadvantages of the prior art. According to this invention, a medical fluid collection device is provided with a barrel which defines a bore. A piston is positioned to slide within the bore, and a pierceable diaphragm is mounted to seal the barrel such that the interior of the bore between the piston and the diaphragm is a sealed volume. Means are provided for manually moving the piston in the bore to create a region of subatmospheric pressure in the barrel, and means are provided for locking the piston in position in the barrel to maintain the subatmospheric pressure in the region.

The fluid collection device of this invention is used by first manually creating a region of subatmospheric pressure in the barrel by withdrawing and locking the piston. Then the device is used in the conventional manner by piercing the diaphragm with a needle and allowing the subatmospheric pressure to draw fluids through the needle into the barrel.

According to a second aspect of the invention, a self-sealing conduit assembly is provided which includes a conduit, such as a needle for example, having at least one sharpened end. A solid pierceable member is positioned around the sharpened end of the conduit, and means are provided for resiliently biasing the member into a first position. In this first position, the solid pierceable member fits over the conduit to block the passage of fluids out of the sharpened end of the conduit. The member is movable into a second position, in which the sharpened end of the conduit is positioned out of the member and fluids are free to pass out of the sharpened end of the conduit.

In use, this conduit assembly provides a self-sealing conduit which facilitates the collection of body fluids such as blood. The pierceable member normally serves to plug the sharpened end of the conduit to prevent the leakage of fluids such as blood. When it is desired to remove fluids through the conduit, the pierceable member can simply be pushed along the conduit to expose the sharpened end of the conduit, thereby opening the conduit. Then, when collection has been completed, the biasing means serves to return the pierceable member to the first position automatically, thereby blocking the further flow of fluids out of the sharpened end of the needle.

This self-sealing conduit assembly provides several important advantages. Because the pierceable member automatically seals the sharpened end of the conduit, the conduit can be connected to a source of fluids, by inserting it into a vein, for example, without allowing the fluid to leak out of the sharpened end of the conduit. However, the conduit can readily be unsealed simply by exerting pressure on the pierceable member to cause the pierceable member to slip down around the conduit to expose the sharpened end of the conduit. Thus, the self-sealing conduit assembly of this invention can readily be sealed and unsealed without manipulating valves or the like.

The self-sealing conduit assembly of this invention is particularly useful in connection with the fluid collection device of this invention. Preferably, the pierceable diaphragm of the fluid collection device is provided with a concave recess shaped to receive the pierceable member of the self-sealing conduit assembly. The pierceable member is preferably provided with a convex surface shaped to fit within the recess of the pierceable diaphragm. Once the conduit is properly placed in a vein, blood can be collected merely by locking the piston in position in the barrel of the collection device to create a subatmospheric pressure in the barrel and then pressing the pierceable diaphragm of the collection device on the pierceable member of the conduit assembly. When pressure is applied to the barrel, the pierceable member is forced down around the conduit exposing the sharpened end of the conduit, which then passes through the pierceable diaphragm into the interior of the collection device. Thus, the sharpened end of the conduit is automatically exposed and unsealed, merely by exerting pressure on the pierceable member.

The invention itself, together with further objects and attendant advantages, will best be understood by reference to the following detailed description taken in connection with the accompanying drawings.

BRIEF DESCRIPTION OF THE DRAWINGS

FIG. 1 is a cross-sectional view of a first preferred embodiment of the fluid collection device of this invention.

FIG. 2 is a cross-sectional view of a first preferred embodiment of the self-sealing conduit assembly of this invention.

FIG. 3 is a sectional view taken along line 3—3 of FIG. 1.

FIG. 4 is a cross-sectional view taken along line 4—4 of FIG. 3.

FIG. 5 is a cross-sectional view of the embodiments of FIGS. 1 and 2, as configured for sample collection.

FIG. 6 is a cross-sectional view of a second preferred embodiment of the fluid collection device of this invention.

FIG. 7 is a cross-sectional view taken along line 7—7 of FIG. 6.

FIG. 8 is a cross-sectional view taken along line 8—8 of FIG. 7.

FIG. 9 is a cross-sectional view taken along line 9—9 of FIG. 8.

FIG. 10 is a cross-sectional view of the rear portion of the embodiment of FIG. 6 showing a pushing member installed.

FIG. 11 is a cross-sectional view taken along line 11—11 of FIG. 10.

DETAILED DESCRIPTION OF THE PREFERRED EMBODIMENTS

Referring now to the drawings, FIG. 1 shows a cross-sectional view of a first preferred embodiment of the medical fluid collection device of this invention. This embodiment, which is indicated generally by the reference numeral 10, includes a barrel 20 which is provided with an open end 22 and a closed end 24. The closed end 24 defines a rectangular opening 26 therein. This rectangular opening 26 defines at one edge thereof a protruding locking member 28, as best shown in FIG. 4. This locking member 28 extends away from the open end 22 of the barrel 20. The barrel 20 defines a cylindrical bore 30 and is provided with a plurality of indicia 32 which serve to mark predetermined volumes of the barrel 20.

A piston 40 is positioned inside the bore 30 of the barrel 20. This piston 40 defines a plurality of sealing rings 42 which slidingly engage the bore 30 to form an airtight seal therewith. A rigid rod 50 is flexibly secured to the piston 40 to extend through the opening 26. This rod 50 is provided with a handle 52 at the end of the rod 50 which passes outside the barrel 20. In addition, the rod 50 defines a plurality of projections 54. As shown in FIGS. 1 and 4, these projections are generally sawtooth in configuration and are shaped to mate with the locking member 28. The interlock provided between the locking member 28 and the projections 54 serves to hold the piston 40 in any one of a number of preselected positions. As shown in FIGS. 3 and 4, the rod can be unlocked from the locking member 28 by moving the rod 50 away from the locking member 28. In this unlocked position, the rod 50 can be moved longitudinally to position the piston 40 as desired in the barrel 20. By simply moving the rod 50 toward the locking member 28, the locking member 28 can be engaged with one of the plurality of projections 54 to lock the rod 50 and therefore the piston 40 in position in the barrel 20.

A pierceable, resilient diaphragm 60 is positioned in the open end 22 of the barrel 20 to seal the barrel 20. This pierceable diaphragm 60 defines an outer concave surface 62 and is made of an elastomeric material which is pierceable by a standard steel hypodermic needle. The diaphragm 60 cooperates with the piston 40 and the barrel 20 to define a sealed interior region 64. In this embodiment, a resilient, annular ring 63 is integrally formed on the outer edge of the concave surface 62 to overhang a portion of the recess defined by the concave surface 62.

FIG. 2 provides a cross-sectional view of a preferred embodiment 70 of the self-sealing conduit assembly of this invention. This embodiment 70 includes a conduit 72, which in this preferred embodiment is a steel hypodermic needle. This conduit 72 defines first and second sharpened ends 74,76, respectively, and the conduit is bent such that the ends 74,76 are parallel but offset to facilitate insertion of the end 74 into the skin of a subject at a shallow angle with the skin. A pierceable elastomeric plug 80 is positioned on the second sharpened end 76 of the conduit 72. This plug 80 is preferably formed of an elastomeric material which is translucent, such that the sharpened end 76 of the conduit 72 can be seen within the plug 80. The outer surface 82 of this plug 80 defines a convex curve shaped to fit within the recess defined by the outer surface 62 of the pierceable diaphragm 60. Additionally the outer surface 82 defines a resilient annular lip 83 sized to fit under and interlock with the annular ring 63 of the diaphragm 60.

A disc 90 is rigidly secured to an intermediate portion of the conduit 72 by means of a layer of epoxy cement 92. A resilient elastomeric sleeve is bonded between the disc 90 and the pierceable plug 80. This sleeve 94 extends completely around the conduit 72, and acts to seal and protect the conduit 72 from contamination. The sleeve 94 resiliently biases the plug 80 into a first, extended position, as shown in FIG. 2. If desired, the sleeve 94 can be provided with preformed fold lines (not shown). In this extended position, the plug 80 serves to block the second end 76 of the conduit 72, and thereby prevents the escape of fluids therefrom.

The use of the fluid collection device 10 and the self-sealing conduit assembly 70 of FIGS. 1 and 2 will now be described in connection with FIG. 5. In order to prepare the collection device 10 for use, the rod 50 is manually moved from the position shown in FIG. 1 to the position shown in FIG. 5, or to a partially withdrawn position. Then the piston 40 is locked in place by engaging the locking member 28 on the appropriate projection 54. This movement of the piston 40 in the barrel 20 develops a subatmospheric pressure within the interior region 64. As will be explained below, this subatmospheric pressure aids in the collection of fluids in the interior region 64.

After a subatmospheric pressure has been created in the interior region 64 of the collection device 10, the self-sealing conduit assembly 70 is then inserted into a superficial vein. As shown in FIG. 5, the first sharpened end section 74 is passed through the skin of a patient into the vein. At this point, the pierceable plug 80 is still situated over the second sharpened 76 as shown in FIG. 2 to prevent the escape of blood from the conduit 72. Because the plug is formed of a translucent or transparent material, it is possible to see the presence of blood at the second sharpened end 72 through the plug 80. In this way, it can be determined that the first sharpened end 74 has been accurately placed within the desired vein, yet significant quantities of blood are not allowed to escape from the conduit 72.

After the conduit assembly 70 has been properly installed in a vein and a subatmospheric pressure has been generated in the interior region 64, the barrel 20 is then positioned with the pierceable plug 80 adjacent the pierceable diaphragm 60. The barrel is then moved in the direction of the disc 90. This movement causes the second sharpened end 76 of the conduit 72 to pass through the pierceable plug and the pierceable diaphragm 60 into the interior region 64. In addition, the lip 83 passes through and interlocks with the ring 63 to hold the plug 80 adjacent the diaphragm 60 with a light holding force. Because both the lip 83 and the ring 63 are resilient, both deform resiliently to allow the lip 83 to pass through the ring 63. Then the subatmospheric pressure inside the interior region 64 draws blood through the conduit 72 into the interior region 64. The plug 80 may be pierced along the line the conduit follows in order to facilitate passage of the sharpened end 76 through the plug.

After the desired quantity of blood has been drawn, the blood can be dispensed from the barrel 20 in one of two ways. One approach is to remove the conduit assembly 70 and the collection device 10 as a unit from the vein. When this is done, the combination of the collection device 10 and the conduit assembly 70 can then be used as a syringe to dispense blood as needed from the interior region 64 into secondary receptacles (not shown). By unlocking the rod 50 from the locking member 28 and then exerting pressure on the handle 52, the piston can be pushed toward the diaphragm 60 to force blood out of the conduit 72.

Alternately, the collection device 10 can be removed from the conduit assembly 70 while the conduit assembly is still inserted in the vein. When this is done, the pierceable diaphragm 60 closes after the conduit 72 has been removed in order to seal blood within the interior region 64. In addition, the resilient sleeve 94 pushes the pierceable plug 80 from the position shown in FIG. 5 to the position shown in FIG. 2. The interlock between the lip 83 and the ring 63 transfers a pulling force from the collection device 10 to the plug 82 which tends to restore the plug 82 to the position of FIG. 2, thereby reducing the need for the sleeve 94 to generate strong spring forces. In this way, the second sharpened end 76 is again sealed to prevent blood leakage out of the conduit 72. The plug 82 provides a wiping action to seal the needle effectively inside the plug 82. Additional blood can then be collected by providing a second fluid collection device 10 and pressing it against the pierceable plug 80 to cause the second sharpened end 76 to pass through the pierceable diaphragm 60 of the second collection device.

In the preferred embodiments of FIGS. 1 and 2, the pierceable diaphragm 60 and the pierceable plug 80 are preferably formed of resilient elastomeric material such as silicone rubber, for example. The rigid components such as the barrel 20 and the rod 50 are formed of conventional plastic materials, such as those used in the manufacture of conventional syringes. The interior region 64 is preferably a sealed, sterile volume.

FIGS. 6-9 shown a second preferred embodiment of the fluid collection device of this invention. This second preferred embodiment is indicated generally by reference numeral 100. This second preferred embodiment includes a barrel 20, a piston 40, and a pierceable diaphragm 60, similar to the respective components of the first preferred embodiment 10 of FIG. 1.

This second preferred embodiment 100 differs from the first preferred embodiment 10 primarily in the means for moving the piston 40 and the means for locking the piston 40 in position. In the second preferred embodiment 100 a flexible cord 110 is coupled to the rear of the piston 40. This cord 110 is provided with a plurality of enlarged balls 112 separated by narrowed neck portions 114. A handle 116 is provided at the extreme end portion of the cord 110. The barrel 20 of this preferred embodiment defines two openings in the rear portion thereof: a first opening 120, and a second opening 122. The first opening 120 is sized to allow the enlarged balls 112 to pass therethrough. The second opening 122 intersects the first opening 120 and is sized to receive the neck portions 114 of the cord 10 but not the enlarged balls 112. The narrowed region 124 between the first and second openings 120,122 is large enough to pass the neck portion 114 of the cord 110.

In order to move and lock the piston 40 of the second preferred embodiment 100, the cord 110 is positioned in the first opening 120 and force is then applied to the handle 116. This causes the cord 110 to move through the first opening 120 and the piston 40 to move in the barrel 20. FIG. 8 shows in solid lines the cord 110 in position in the first opening 120. Then, after the piston 40 has been positioned as desired, the cord 110 is moved into the second opening 122. This second position of the cord 110 is shown in dotted lines in FIG. 8 and in FIG. 9. Once the cord 110 has been placed in the second opening 122, the subatmospheric pressure behind the piston 40 pulls the adjacent enlarged ball against the outer edge of the second opening 122, thereby locking the piston 40 in position. The second preferred embodiment 100 is used similarly to the first preferred embodiment 10.

FIGS. 10 and 11 show the use of a rigid pushing member 140, which includes a crescent-shaped channel 142 sized to fit around the cord 110 and the balls 112 and to fit within the first opening 120 to bear on the piston 40. The pushing member 140 terminates in a handle 144. Once the barrel 20 has been filled with fluid, the pushing member 140 can be inserted through the first opening 120 and used to push the piston 40 towards the diaphragm 60 to dispense fluid from the barrel 20.

From the foregoing, it should be apparent that a new and improved fluid collection system has been described. This system comprises a novel collection device which can be used with a novel self-sealing conduit assembly. The novel collection device provides the important advantages that subatmospheric pressure is manually generated just prior to use in the fluid receiving chamber. In this way the problems of leakage, contamination, and low shelf life are minimized. In addition, because the piston of the collection device can be positioned in any one of a number of preselected positions, it is readily possible to use this collection device for collecting blood samples of any one of a number of predetermined volumes. In this way the need for multiple collection devices of different volumes is reduced. The self-sealing conduit assembly of this invention provides the important advantage that it automatically seals the conduit to prevent unwanted leakage of fluids out of the conduit during times when the conduit is not coupled to a fluid collection device.

Of course, it should be understood that various changes and modifications to the preferred embodiments described above will be apparent to those skilled in the art. For example, other elastomeric materials can be used, and the capacity of the fluid collection device can be varied as necessary to accomodate the desired volume of collected fluid. In addition, in some applications it may be preferable to use other types of locking means for the piston. Furthermore, the diaphragm can be made of a flexible material which assumes the desired concave shape in response to the vacuum developed in the collection device, or the diaphragm can be provided with a convex shape and the plug with a matching concave shape. Alternately, the barrel can be provided with a rectangular cross-section, with one of the wider sides adapted to be placed against the skin of a subject to facilitate the insertion of the needle at a shallow angle with respect to the skin of the subject. Such changes and modifications can be made without departing from the spirit and scope of the present invention and without diminishing its attendant advantages. It is therefore intended that all such changes and modifications be covered by the following claims.

We claim:

1. A medical fluid collection device comprising:
   means for defining a fluid collection chamber;
   means for manually generating a subatmospheric pressure in the chamber, said generating means comprising a handle mechanically secured to a portion of the chamber defining means to allow manual positioning of said portion with respect to the remainder of the chamber defining means by manipulation of the handle;
   a pierceable diaphragm mounted to the chamber defining means such that a first side of the diaphragm is in fluid communication with the chamber; and
   means for mechanically locking the portion of the chamber defining means in place with respect to the remainder of the chamber defining means to maintain subatmospheric pressure in the chamber.

2. The invention of claim 1 wherein the chamber defining means comprises a barrel and a piston slidingly mounted in the barrel.

3. The invention of claim 2 wherein the locking means comprises means for mechanically locking the handle to the barrel to maintain subatmospheric pressure in the barrel.

4. The invention of claim 1 wherein the diaphragm defines a recess and a resilient, annular ring positioned partially to overhang the recess.

5. A medical fluid collection device comprising:
   a barrel defining a bore;
   a piston sealingly and slidingly positioned in the bore;
   a pierceable diaphragm mounted to seal the barrel adjacent the bore such that the interior of the bore between the piston and the diaphragm is a sealed volume,
   means, mechanically connected to the piston and comprising a handle which extends out of the bore, for manually moving the piston in the bore to create a region of subatmospheric pressure in the barrel; and
   means, secured to the barrel, for mechanically locking the piston in position in the barrel to maintain subatmospheric pressure in the region.

6. The invention of claim 5 wherein the moving means comprises a rod attached to the piston such that the rod extends outside of the barrel.

7. The invention of claim 6 wherein the locking means comprises at least one projection secured to the rod and a locking member secured to the barrel and positioned to engage the projection.

8. The invention of claim 5 wherein the moving means comprises a flexible cord attached to the piston to extend out of the barrel.

9. The invention of claim 8 wherein the locking means comprises at least one enlarged portion included in the cord and a receiving recess included in the barrel and sized to receive and retain the enlarged portion.

10. The invention of claim 5 wherein the diaphragm defines a recess and a resilient, annular ring positioned partially to overhang the recess.

11. A self-sealing conduit assembly comprising:
    a conduit having at least one sharpened end;
    a pierceable member positioned in a first position to contact the sharpened end of the conduit to block the flow of fluid therefrom;
    means for resiliently biasing the member into the first position, said member movable to a second position, in which the sharpened end of the conduit is positioned out of the member and fluids are free to pass out of the sharpened end of the conduit.

12. The invention of claim 11 wherein the conduit is a needle having two sharpened ends.

13. The invention of claim 11 wherein the biasing means comprises:
    a positioning member secured to the conduit; and
    a resilient sleeve secured at one end to the positioning member and at the other end to the pierceable member such that the sleeve extends around and seals a portion of the conduit.

14. The invention of claim 11 wherein the pierceable member is translucent such that the conduit is visible within the pierceable member.

15. The invention of claim 11 wherein the pierceable member defines a convex outer surface over the sharpened end of the conduit and a resilient lip positioned around the convex outer surface.

16. A self-sealing conduit assembly comprising:
    a double ended needle;
    a disc secured to an intermediate portion of the needle;
    a resilient sleeve secured to the disc to extend around a portion of the needle;
    a pierceable, translucent plug secured to the sleeve such that the plug is positioned to contact and seal one end of the needle in an extended position to prevent fluids from leaking therefrom, said plug being moveable along the needle to a retracted position in which the one end of the needle extends out of the plug;
    said sleeve acting to bias the plug into the extended position.

17. The invention of claim 16 wherein the plug defines a convex outer surface over the sharpened end of the conduit and a resilient lip positioned around the convex outer surface.

18. A medical fluid collection system comprising:
    a conduit having at least one sharpened end;
    a pierceable member positioned around the sharpened end of the conduit;
    means for resiliently biasing the member into a first position, in which the member serves to block the passage of fluids out of the sharpened end of the conduit, such that the member is movable to a second position, in which the sharpened end of the conduit is positioned out of the member and fluids are free to pass out of the sharpened end of the conduit;
    a barrel defining a bore;
    a piston sealingly and slidingly positioned in the bore;
    a pierceable diaphragm mounted to seal the barrel adjacent the bore such that the interior of the bore between the piston and the diaphragm is a sealed volume;

means for manually moving the piston in the bore to create a region of subatmospheric pressure in the barrel;

means for locking the piston in position in the barrel to maintain the subatmospheric pressure in the region;

the pierceable member shaped to fit against the pierceable diaphragm such that pressure on the barrel acts to move the pierceable member to the second position and to push the sharpened end of the conduit through both the pierceable member and the pierceable diaphragm into the interior of the bore;

means, included in the barrel, for retaining the pierceable member against the diaphragm;

the biasing means acting to bias the pierceable member to the first position after the pierceable diaphragm has been removed from the conduit.

19. A medical fluid collection system comprising:
a double ended needle;
a disc secured to an intermediate portion of the needle;
a resilient elastomeric sleeve secured to the disc to extend around a portion of the needle;
a pierceable, translucent plug secured to the sleeve such that the plug is situated around and in contact with one end of the needle in an extended position to prevent fluids from leaking therefrom, said plug having a convex outer surface adjacent the one end of the needle and a resilient lip positioned around the convex outer surface, said plug being movable along the needle to a retracted position in which the one end of the needle extends out of the plug, said sleeve acting to bias the plug into the extended position;
a barrel defining a bore;
a piston slidingly and sealingly positioned in the bore;
a pierceable diaphragm secured to the barrel to seal an interior volume of the bore between the piston and the diaphragm, said diaphragm defining a recess shaped to receive and position the outer surface of the plug such that, when the plug is positioned in the recess and the barrel is urged toward the disc, the one end of the needle passes through the plug and the diaphragm into the interior volume of the barrel;
means, mounted adjacent the diaphragm, for interlocking with the lip on the plug to provide a holding force tending to secure the plug adjacent the diaphragm;
means for manually moving the piston in the barrel away from the diaphragm to reduce the pressure in the interior volume; and
means for locking the piston in a selected position to maintain a reduced pressure in the interior volume.

20. The invention of claim 18 or 19 wherein the moving means comprises a rod attached to the piston such that the rod extends outside of the barrel.

21. The invention of claim 26 wherein the locking means comprises at least one projection secured to the rod and a locking member secured to the barrel and positioned to engage the projection.

22. The invention of claim 18 or 19 wherein the moving means comprises a flexible cord attached to the piston to extend out of the barrel.

23. The invention of claim 22 wherein the locking means comprises at least one enlarged portion included in the cord and a receiving recess included in the barrel and sized to receive and retain the enlarged portion.

24. The invention of claim 19 wherein the interlocking means comprises a resilient, annular ring positioned to overhang partially the recess to engage the lip.

25. The invention of claim 1 further comprising means, mounted adjacent a second side of the pierceable diaphragm, for releasably retaining a double ended needle in place with respect to the diaphragm.

26. The invention of claim 5 further comprising means, mounted adjacent a second side of the pierceable diaphragm, for releasably retaining a double ended needle in place with respect to the diaphragm.

27. A medical fluid collection system comprising:
a double ended needle;
a disc secured to an intermediate portion of the needle;
a resilient elastomeric sleeve secured to the disc to extend around a portion of the needle;
a pierceable, translucent plug secured to the sleeve such that the plug is situated around and in contact with one end of the needle in an extended position to prevent fluids from leaking therefrom, said plug having a substantially spherical outer surface adjacent the one end of the needle and a resilient lip positioned around said outer surface, said plug being movable along the needle to a retracted position in which the one end of the needle extends out of the plug, said sleeve acting to bias the plug into the extended position;
a barrel defining a bore;
a piston slidingly and sealingly positioned in the bore;
a pierceable diaphragm secured to the barrel to seal an interior volume of the bore between the piston and the diaphragm, said diaphragm defining a substantially concave recess shaped to receive and position the outer surface of the plug such that, when the plug is positioned in the recess and the barrel is urged toward the disc, the one end of the needle passes through the plug and the diaphragm into the interior volume of the barrel;
means mounted adjacent the diaphragm, for interlocking with the lip on the plug to provide a holding force tending to secure the plug adjacent the diaphragm;
means for manually moving the piston in the barrel away from the diaphragm to reduce the pressure in the interior volume; and
means for locking the piston in a selected position to maintain a reduced pressure in the interior volume.

28. A medical fluid collection device comprising:
means for defining a fluid collection chamber;
means for manually generating a subatmospheric pressure in the chamber;
a pierceable diaphragm mounted to the chamber defining means such that a first side of the diaphragm forms a side of the chamber; and
means for locking the generating means in place at different, selectable locations to maintain subatmospheric pressure in the chamber and to provide different volumes in said collection chamber.

29. The invention of claim 28 wherein the chamber defining means comprises a barrel and a piston slidingly mounted in the barrel.

30. The invention of claim 29 wherein the means for generating a subatmospheric pressure comprises a handle secured to the piston and means for locking the piston in position in the barrel.

31. The invention of claim 28 wherein the diaphragm defines a recess and a resilient, annular ring positioned partially to overhang the recess.

32. The invention of claim 28, further comprising means, mounted adjacent a second side of the pierceable diaphragm, for releasably retaining a double-ended needle in place with respect to the diaphragm.

33. A medical fluid collection device comprising:
a barrel defining a bore;
a piston sealingly and slidingly positioned in the bore;
a pierceable diaphragm mounted to seal the barrel adjacent the bore such that the interior of the bore between the piston and the diaphragm is a sealed volume;
means for manually moving the piston in the bore to create a region of subatmospheric pressure in the barrel; and
means for locking the piston in position in the barrel at different selectable locations to maintain subatmospheric pressure in the region and to provide different capacities of sealed volume in the bore.

34. The invention of claim 33 wherein the moving means comprises a rod attached to the piston such that the rod extends outside the barrel.

35. The invention of claim 34 wherein the locking means comprises at least one projection secured to the rod and a locking member secured to the barrel and positioned to engage the projection.

36. The invention of claim 33, further comprising means, mounted adjacent to a second side of the pierceable diaphragm, for releasably retaining a double-ended needle in place with respect to the diaphragm.

37. A medical fluid collection device comprising:
means for defining a fluid collection chamber;
means for manually generating a subatmospheric pressure in the chamber; and
a pierceable diaphragm mounted to the chamber defining means such that a first side of the diaphragm is in fluid communication with the chamber;
said diaphragm defining a recess and a resilient, annular ring positioned partially to overhang the recess.

38. A medical fluid collection device comprising:
a barrel defining a bore;
a piston sealingly and slidingly positioned in the bore;
a pierceable diaphragm mounted to seal the barrel adjacent the bore such that the interior of the bore between the piston and the diaphragm is a sealed volume;
means for manually moving the piston in the bore to create a region of subatmospheric pressure in the barrel; and
means for locking the piston in position in the barrel to maintain subatmospheric pressure in the region;
said moving means comprising a flexible cord attached to the piston to extend out of the barrel.

39. The invention of claim 38 wherein the locking means comprises at least one enlarged portion included in the cord and a receiving recess included in the barrel and sized to receive and retain the enlarged portion.

40. A medical fluid collection device comprising:
a barrel defining a bore;
a piston sealingly and slidingly positioned in the bore;
a pierceable diaphragm mounted to seal the barrel adjacent the bore such that the interior of the bore between the piston and the diaphragm is a sealed volume;
means for manually moving the piston in the bore to create a region of subatmospheric pressure in the barrel; and
means for locking the piston in position in the barrel to maintain subatmospheric pressure in the region;
said diaphragm defining a recess and a resilient, annular ring positioned partially to overhang the recess.

* * * * *